(12) United States Patent
Yamagata et al.

(10) Patent No.: US 7,687,031 B2
(45) Date of Patent: Mar. 30, 2010

(54) MICROCHIP

(75) Inventors: Yutaka Yamagata, Wako (JP); Kozo Inoue, Shibuya-ku (JP)

(73) Assignee: Fuence Co., Ltd., Tokyo (JP)

( * ) Notice: Subject to any disclaimer, the term of this patent is extended or adjusted under 35 U.S.C. 154(b) by 993 days.

(21) Appl. No.: 10/467,805

(22) PCT Filed: Feb. 14, 2002

(86) PCT No.: PCT/JP02/01268

§ 371 (c)(1),
(2), (4) Date: Feb. 13, 2004

(87) PCT Pub. No.: WO02/065138

PCT Pub. Date: Aug. 22, 2002

(65) Prior Publication Data

US 2004/0121356 A1    Jun. 24, 2004

(30) Foreign Application Priority Data

Feb. 14, 2001  (JP) .............................. 2001-037147

(51) Int. Cl.
*B01L 11/00*  (2006.01)
(52) U.S. Cl. .............................. 422/100; 506/13; 506/7
(58) Field of Classification Search .................. None
See application file for complete search history.

(56) References Cited

U.S. PATENT DOCUMENTS

| | | | | |
|---|---|---|---|---|
| 5,681,484 A | * | 10/1997 | Zanzucchi et al. | ............ 506/40 |
| 6,074,827 A | * | 6/2000 | Nelson et al. | ................... 435/6 |
| 6,140,144 A | * | 10/2000 | Najafi et al. | ................... 438/53 |
| 6,350,609 B1 | * | 2/2002 | Morozov et al. | ......... 435/283.1 |
| 6,548,263 B1 | * | 4/2003 | Kapur et al. | ................... 506/32 |
| 6,653,089 B2 | * | 11/2003 | Takayama et al. | .......... 435/7.72 |
| 6,660,517 B1 | * | 12/2003 | Wilding et al. | ........... 435/289.1 |

FOREIGN PATENT DOCUMENTS

EP    0 430 248 A2    6/1991

(Continued)

OTHER PUBLICATIONS

V. Morozov et al., "Electrospray Deposition as a Method For Mass Fabrication Of Mono- and Multicompontent Microarrays of Biological and Biologically Active Substances," *Analytical Chemistry*, vol. 71. No. 15, pp. 3110-3117, Aug. 1999.

Baba, "Hito-genome Keikaku no Mukou ni Mierumono Kagaku no Hatasu Yakuwari", Chemistry, Apr. 1, 2000, vol. 55 No. 4, pp. 22-26.

(Continued)

*Primary Examiner*—Jeffrey S. Lundgren
(74) *Attorney, Agent, or Firm*—Oliff & Berridge, PLC

(57) ABSTRACT

A microchip is provided, the microchip comprises a block constituting a reaction system, wherein said reaction system includes: a reaction region including biomolecules immobilized therein in form of a spot(s) or a strip(s); a supply flow channel connected to the reaction region for supplying a sample solution; and a recovery flow channel connected to the reaction region for recovering the sample solution which passes through at least a part of the reaction region. Thereby bonds or bindings between the biomolecules or biomacromolecules and the samples can be detected on the microchip using the slight quantity of both the sample and the biomolecules.

10 Claims, 8 Drawing Sheets

FOREIGN PATENT DOCUMENTS

| | | |
|---|---|---|
| EP | 0 969 083 A1 | 1/2000 |
| JP | A 11-75812 | 3/1999 |
| WO | WO 98/58745 | 12/1998 |
| WO | WO 00/04382 | 1/2000 |
| WO | WO 00/73766 A1 | 12/2000 |

OTHER PUBLICATIONS

Morozov, V.N. et al, "New polyacrylamide gel-based methods of sample preparation for optical micrscopy: immobilization of DNA molecules for optical mapping", Journal of Microscopy, Sep. 1996; pp. 205-214.

* cited by examiner

FIG. 7
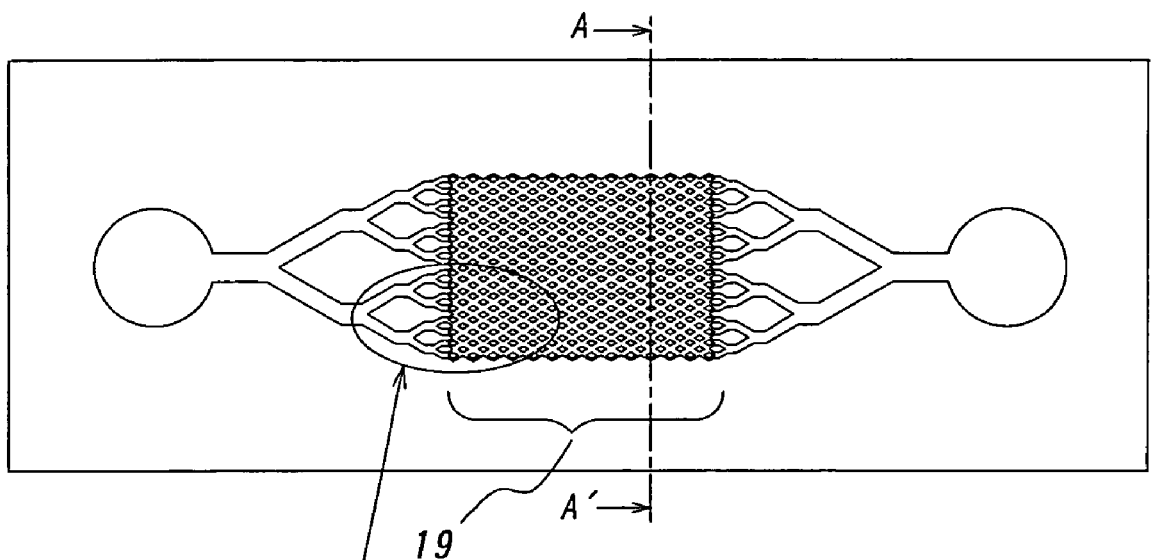
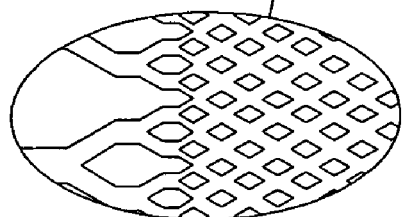
Enlarged view
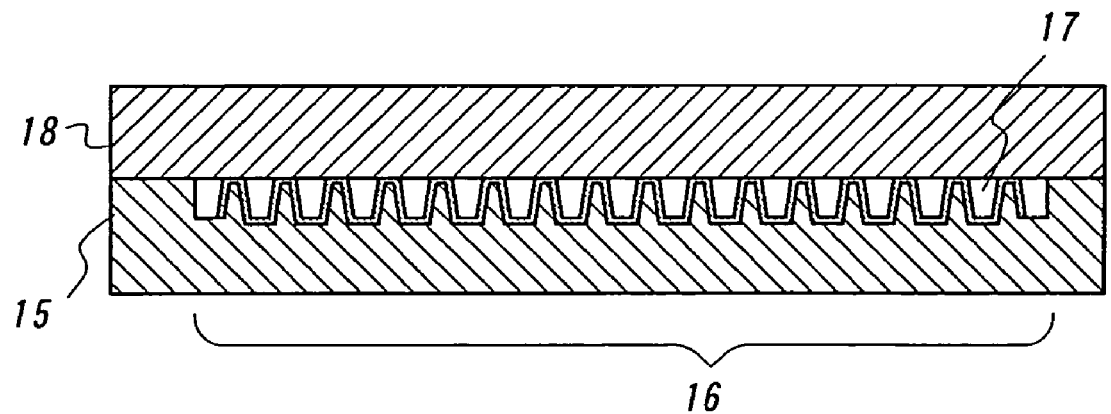
A-A' section view

MICROCHIP

BACKGROUND OF THE INVENTION

1. Field of the Invention

The present invention relates to a microchip comprising biomolecules such as proteins or nucleic acids, and more particularly to a microreactor comprising a plurality of reaction systems utilizing the microchip.

2. Related Art Statements

Sequencing of human genome has been completed owing of progress in human genome researching. Although the complete sequencing of the human genome is very important achievement of life science, this is only the beginning of further problems. The importance issues of fundamental and applied research have already shifted to investigation of functions of individual genes, i.e. the functions of proteins produced by the individual genes. Investigation of individual gene expression mechanism is very important as well as the investigation of functions. Anyway, to investigate such problems, a technology that many kinds of samples or minute amount of samples can simultaneously analyzed is essential for execution of these investigations.

A microarray i.e. microchip technology has attracted attention as an important technology which makes possible to implement the purposes and is developing rapidly. A photolithography, a mechanical-spotting method, and an inkjet method, etc. as a manufacturing technology of DNA microarrays, have been in practical use (refer to a document "Trends in Biotechnology, 16", 1998, pp. 301-306). In addition, some technologies, that bondings or bindings between a number of proteins and ligands can simultaneously be detected, are going to be developed. The technologies are followings: a microchip technology combining with a mass spectrometry (refer to a document "Mass Spectrometry Reviews, 16", 1997, pp. 1-23); an acrylamide gel pad method (refer to a document "Anal. Biochem., 278", 2000, pp. 123-131); a polyvinylidene difluoride membrane method (refer to a document "Anal. Biochem., 270", 1999, pp. 103-111); and a two-hybrid assay (refer to a document "Nature, 403", 2000, pp. 623-627), etc. As a method applicable to both DNAs and proteins, an electrospray deposition method is disclosed (refer to a document "Anal. Chem. 71", 1999, pp. 3110-3117).

On the other hand, a technology that a variety of chemical reactions are performed on a microchip using minute amount of samples, which is referred to as "Lab-On-Chip" or "Integrated-Chip", is studied for various purposes. A part of the technology has reached a stage of practical use (refer to Japanese documents and a web site "Pharmacia, 36", 2000, pp. 34-38; "Chemical (Kagaku), 54(10)", 1999, pp 14-19; and http://www/calipertech.com/welcome.html, etc.).

In order to know a hybridization condition of a gene (i.e. amount of production of mRNA), hybridization must be detected using a labeling compound such as a fluorescent material. Thereby detecting bonds on the DNA microchip and identification of bonded substances can be performed at the same time. In case of proteins if both a targeted protein or DNA, and a ligand which bonds with that target material are known and antibodies to the substances are available, both detection and identification of a targeted substance can be performed on the proteins microchip at the same time using a conventional enzyme label immunoassay or an fluorescence immunoassay.

However, if functions or structures of either or both a protein and a compound which combines with the protein are unknown, a separate device or technique must be required for detection of bonds or bindings and identification of the substance which is generated by the bonds, respectively. In order to identify a compound(s) which is generated by combination with the protein, after detection of bonds about the compound on the microchip, the compound must be extracted to be analyzed in various tests. For a DNA microchip, when it is desired to investigate factors of regulation of gene expression, similar process is needed.

OBJECTS OF THE INVENTION

It is an object of the present invention to provide a biomolecules/biomacromolecules microchip having a structure that bonds between many number of proteins or DNAs and compounds can be detected on the chip and the compounds which combine or bind with the proteins can be recovered to be identified.

It is another object of the present invention to provide a microreactor that a particular compound can be generated from an original compound in successively reaction using reaction regions, on which a series of enzymes are immobilized thereto, and which reaction regions are connected to each other. In consideration of prevention of environment pollution or global warming and depletion of oil resources, conversion from a conventional organic synthesis process using oils to a biochemical process is very important issue. Here, in order to search for an optimal reaction condition or prepare samples for screening stage, it is very important to establish an enzyme reaction system on a microchip.

It is still another object of the present invention to provide a system for purifying minute amount of biomolecules or biomacromolecules. When various compounds such as proteins are separated and purified, in general available quantity of the sample is very small amount. Such a separation and purification are usually done with electrophoresis or many kinds of chromatography. The electrophoresis is in practical use for using a very small amount of sample. However, the chromatography has not been developed to deal with a very small amount of sample, yet. If the chromatography technology, in which the sample of very small quantity can be processed, were practical in use, it would be very significant. If so, in all experimental processes, facilities would be miniaturized to amazingly reduce times, costs, and labor hours.

In order to attain the objects described above, It is indispensable to certainly fix or immobilize biomolecules, such as proteins or DNAs, or various organic compounds onto a substrate without damage of its functions and to repeat the immobilizing process in high probability. It is preferable that shape, size, number, or density of a structure body immobilized the samples can be change whenever possible according to need. As described in PCT publication WO98/58,745, the electrospray deposition method fits the requirements. Accordingly, detecting bonds or bindings between known proteins or DNAs and ligands and identification of the bonded compounds can simultaneously be done on the microchip, which is manufactured by the electrospray deposition method, using the enzyme label immunoassay or the fluorescence immunoassay with antibodies to them.

On the other hand, it is increasingly important to investigate proteins whose functions are unknown. Although in a gene level certain gene is presumed to serve as certain role in a living body, it is not enough. First and foremost, functions of a protein, which are coded by its gene, must be clarified. Therefore, various approaches have been proposed. For example, there is a method of presuming the functions based on similarity with known proteins by using clarifying partial structures, such as core of activity, by NMR (nuclear magnetic resonance equipment). There is a fact that all reactions in a living body are triggered by combination with a ligand(s) and are performed by proteins. Taking account of the fact, it goes without saying that the most important and direct way to clarify proteins whose functions are unknown is firstly to find out a substance which bonds or binds with the protein and then to clarify a structure of the substance which bonded with the protein.

To that end, it must firstly be detected whether a protein is combined with a test compound on a protein microchip having the immobilized protein therein using the electrospray deposition method. An optimal detection technique is suitably selected depending on combination of a protein with a compound. If there is a compound which bonded or bound with the protein, this compound is and recovered and disassociated from the protein. Then a structure of the compound is determined using various analytical techniques. The present invention aims to provide and disclose a microchip (i.e. microreactor) which achieve such functions.

In addition, in order to manufacture a microreactor, it is preferable that a necessary group of enzymes is immobilized onto predetermined locations respectively and which locations are connected to each other. In addition, so as to refine a minute amount of compound, a substance, which preferentially associates with a targeted compound, or a substance, which is used by various conventional chromatographies, is immobilized. Thereby different types of chromatography devices can be manufactured. In this regard, a structure body which is immobilized may suitably be selected for any purpose. In one instance, the structure body may be immobilized over the length and breadth of flow channels or may be immobilized in form of porous by varying the condition of the electrospray deposition.

SUMMARY OF THE INVENTION

According to the present invention, a microchip comprises a block constituting a reaction system,
wherein said reaction system includes:
a reaction region including biomolecules immobilized therein in form of a spot(s) or a strip(s);
a supply flow channel connected to the reaction region for supplying a sample solution; and
a recovery flow channel connected to the reaction region for recovering the sample solution which passes through at least a part of the reaction region.

According to the present invention, bonds or bindings between the biomolecules or biomacromolecules and the samples can be detected on the microchip using the slight quantity of both the sample and the biomolecules. In addition a compound(s), which is generated through the bindings or the reaction, may be collected by the recovery flow channel and is recovered to be identified.

In a preferable embodiment of the microchip according to the present invention, said block is formed by a first and a second substrates which are bonded mutually such that the reaction region, the supply flow channel and the recovery flow channel are formed at a boundary, more properly a gap, between flat surfaces of the first and second substrates; and said block further comprises an inlet and an outlet for communicating the supply flow channel and recovery flow channel to outside.

According to the present invention, for example, a microchip can be manufactured in a simple manufacturing method such that a first plate having a concave potion is bonded with a second plate, on which biomolecules are fixed or immobilized thereon.

In another embodiment of the microchip according to the present invention, said biomolecules are immobilized using an electrospray deposition method.

According to the invention, the spot of the biomolecules or biomacromolecules can be immobilized using the electrospray deposition method without any damage of biological functions of the biomolecules.

In still another embodiment of the microchip according to the present invention, said supply flow channel and said recovery flow channel are arranged in two or three dimensions.

According to the invention, when the flow channels are configured in three dimensions, the sample solution, after which reacts with a particular biomolecules spot, is individually collected and is recovered to be analyzed. In addition, a reaction system in single-input and multiple-output, a reaction system in multiple-input and single-output, or a reaction system in multiple-input and multiple-output can easily be manufactured. When the sample solution is supplied to the spot(s) i.e. reaction region(s) in two dimensions (flat-way style), if there is enough margin for providing minute flow channels, above described reaction system may be implemented. However, when the spots are closely disposed in form of an array on a plane surface, the chip is to be deficient in an area for locating each of the flow channels. Consequently, the flow channels are disposed in three dimensions. For example, when through holes from the bottom to top surface are provided in both or either the first or second of the substrate, the sample solution may be supplied from above or below and is recovered. Thus, even if the spots are closely disposed, each of the flow channels may easily be disposed in the chip.

In still another embodiment of the microchip according to the present invention, said supply flow channel or said inlet comprises a liquid feeder for controlling of supply and/or flow rate of the sample solution, said recovery flow channel or said outlet comprises a liquid recovery device for collecting and recovering the sample solution which passes through the reaction region.

According to the invention, flow rate of the sample solution can be controlled based on characteristics of reactions. In addition reaction product(s) can readily be collected and recovered using the recovering device.

In still another embodiment of the microchip according to the present invention, said reaction system includes:

said supply flow channel, which is single on a side of the inlet and is separated into a plurality of supply flow channels on a side of the reaction region;

said reaction region, which comprises a plurality of paths which are respectively connected to the plurality of flow channels one by one;

said recovery flow channel, which is a plurality of recovery flow channels which are respectively connected to the paths one by one; and said outlet, which is a plurality of outlets which are provided for communicating respectively the plurality of recovery flow channels to outside one by one.

In still another embodiment of the microchip according to the present invention, said reaction system includes:

said supply flow channel, which is single on a side of the inlet and is separated into a plurality of supply flow channels on a side of the reaction region;

said reaction region, which comprises a plurality of paths which are respectively connected to the plurality of supply flow channels one by one; and said recovery flow channel, which is separated into a plurality of recovery flow channels on a side of the reaction region and are interconnected into single recovery flow channel on a side of the outlet.

In still another embodiment of the microchip according to the present invention, said reaction system includes:

said supply flow channel, which is a plurality of supply flow channels;

said inlet, which is a plurality of inlets, wherein the plurality of inlets is connected to the plurality of supply flow channels on a one-to-one basis;

said reaction region, which comprises a plurality of paths;

said recovery flow channel, which is a plurality of recovery flow channels, wherein the plurality of recovery flow channels is connected to the plurality of paths one by one; and said outlet, which is a plurality of outlets which are provided for communicating respectively the plurality of flow channels with outside one by one.

In still another embodiment of the microchip according to the present invention, said reaction system includes:

said supply flow channel, which is a plurality of supply flow channels;

said inlet, which is a plurality of inlets which are provided for communicating respectively the plurality of flow channels with outside one by one;

said reaction region, which comprises a plurality of paths which are respectively connected to the plurality of flow channels one by one; and said recovery flow channels, which is separated into a plurality of recovery flow channels on a side of the reaction region and are interconnected into single recovery channel on a side of the outlet.

As described above, when various reaction system is configured such as in single-input and multiple-output, in multiple-input and single-output, or in multiple-input and multiple-output, the spots can be disposed in form of various styles and the spots arrangement can flexibly respond to a desired reaction. For example, when the microchip is configured in single-input and multiple-output, reaction products can be recovered from each of the spots separately. If the microchip is configured in multiple-input and multiple-output, the reaction system having a many number of reaction paths can be configured to be supplied various kinds of sample solutions at one operation to be recover a reaction product(s) every sample.

In addition, in the present invention, the biomolecules can be immobilized onto arbitrary locations. For example, the biomolecules can be immobilized onto a surface of the first substrate in form of a spot(s). Alternatively, the biomolecules or biomacromolecules may be immobilized onto whole internal surface of the reaction region(s). When this configuration is chosen, owing to enlarging an area of contact surface between the biomolecules and samples, it is possible to increase reaction efficiency of them.

In still another embodiment of the microchip according to the present invention, the number of said reaction systems are equal to or greater than 10, 100, or 1000 systems per $cm^2$.

According to the invention, because the reaction system is miniaturized, the reaction system can be configured in a minute amount of the sample. Additionally, a multi-step reaction can be done on a small area of the single microchip at one operation.

BRIEF DESCRIPTION OF THE DRAWINGS

FIG. 7 is a schematic diagram and its A-A' cross-sectional view depicting a micro-column having biomolecules spots which are immobilized using the electrospray deposition method.

DETAILED DESCRIPTION OF THE PREFERRED EMBODIMENTS

Several preferred embodiments of the microchip according to the present invention will be described with reference to the accompanying drawings. The microchip according to the present invention comprises: a spot(s) or a film(s), wherein organic polymer material or biomolecular material or such as proteins is immobilized using the electrospray deposition method; a supporting part for supporting the spots thereon; micro supply flow channels for supplying a liquid(s) to the spot(s); and micro recovery flow channels for recovering a reaction product(s).

Figure 1:
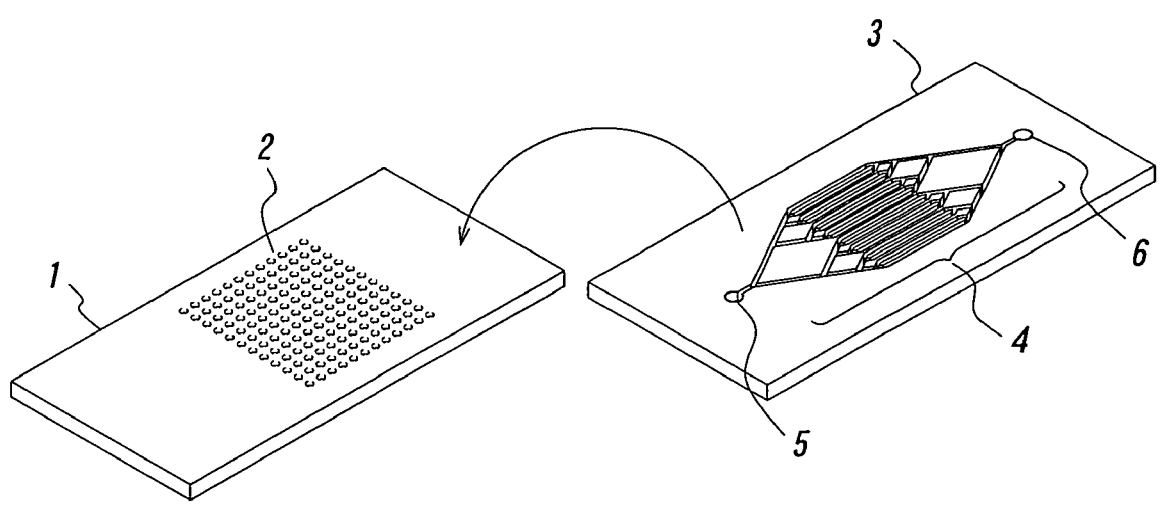
FIG. 1 is an exploded diagram showing a microchip according to the present invention.

FIG. 1 is an exploded diagram showing a microchip according to the present invention. In FIG. 1, a substrate 1 is made of: plastics (PMMA, polycarbonate, polyethylene, fluorocarbon resin, or metal etc.); glass (silica grass, or optical grass, etc.); ceramics (alumina, zirconium oxide, silicon nitride, or aluminum nitride, etc.); or metal. When the substrate is highly electrical insulating material, a thin layer (which is made of gold, platinum, or ITO, etc.) can be coated on the surface of the substrate.

An array of biomolecules spots 2 are formed on the first substrate 1 made of glass or plastics using the electrospray deposition (ESD) method. The array of plurality of spots 2 are formed using a micro-array manufacturing technique (which is disclosed by a document ("Anal. Chem. 71", 1999, pp. 3110-3117)), then the spots 2 are immobilized by treatment with a crosslinking agent (glutaric aldehyde). Various proteins (enzymes, antibodies, membrane proteins, etc.) organic polymer material (acrylate resin, cellulose, ion exchange resin, or epoxy resin, etc.), or dye, etc. can be used in this invention as a material of the spots. Also, most of functional materials, which may be polymerized with cross-linking agent to be immobilized, can be used in this invention.

A second substrate 3 has a concave portion 4 in one surface thereof. The one surface, having the concave potion 4. of the second substrate 3 is bonded to a surface, having spots 2, of the first substrate 1. Owing to the bonding, closed micro flow channels and reaction regions are built between the substrates or in a gap therebetween. Liquid to react with is then to be properly supplied to them. Both ends of the concave potion 4 of the second substrate 3 have through holes respectively, which holes are used as an inlet 5 for supplying liquid and an outlet 6 for recovering the liquid, respectively. The microchip is designed such that the liquid poured into the inlet 5 is supplied to the micro supply flow channels, in which one flow channel is diverged into a number of channels, to uniformly be fed to all spots in parallel. In addition in the microchip, after the branched liquid passes through the spots it would be collected into one flow recovery channel along with confluence of the channels to be recovered from the outlet 6. In other words, the microchip is configured in a reaction system of one-input and multi-output.

Figure 2:
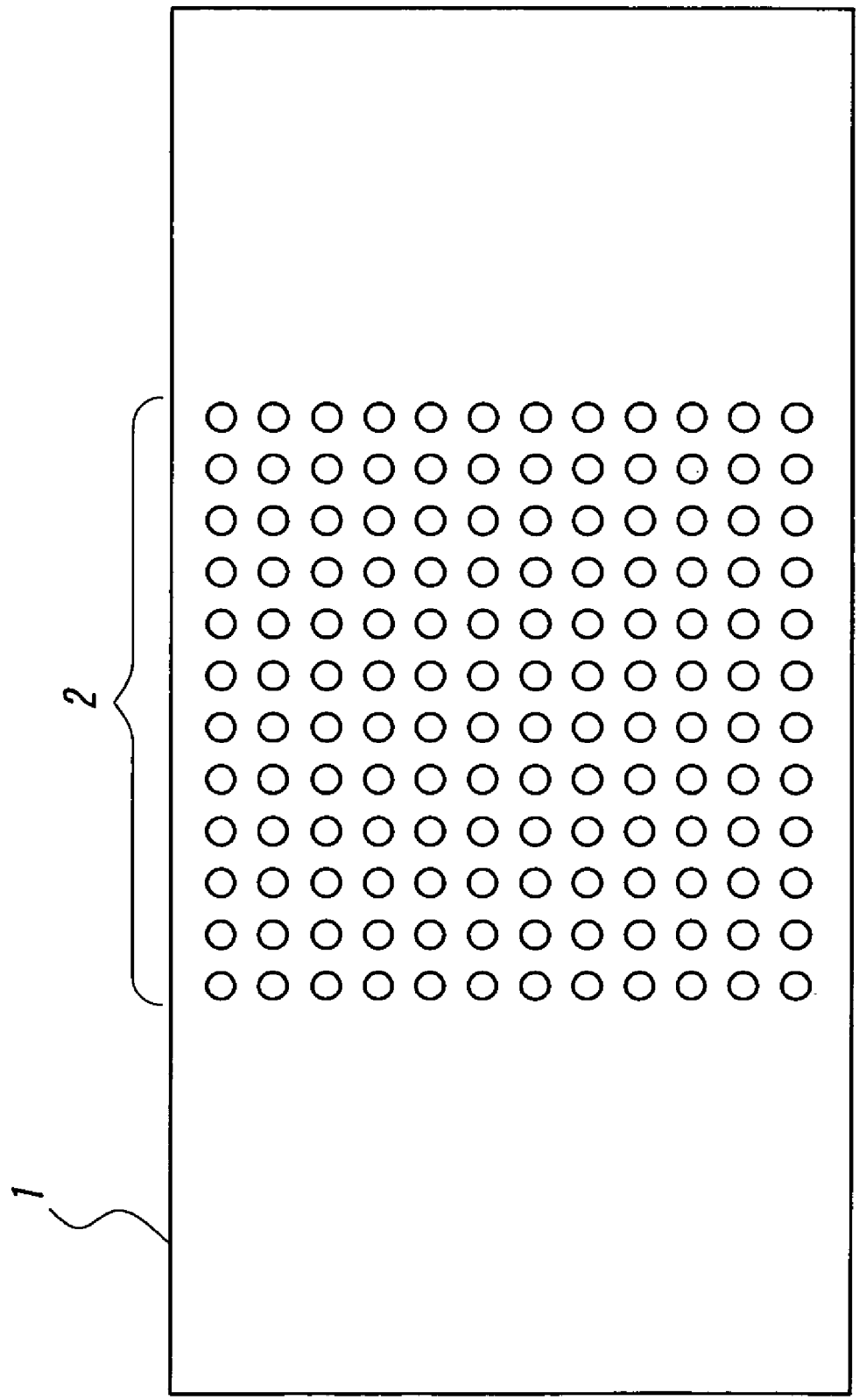
FIG. 2 is a diagram illustrating an arrangement of biomolecules spots 2 formed on a substrate 1.

A structure of the substrate 1, in which biomolecules are immobilized as spots thereon, will be explained in detail. FIG. 2 is a diagram illustrating an arrangement of biomolecules spots 2 formed on the substrate 1. The spots 2 have a diameter of approximately ten to several hundred micronmeters and a thickness of approximately 1-50 micron-meters. The spots 2 are placed at intervals, which are approximately 1-10 fold of the diameter thereof. Number of spots can be in a range from several to several ten thousand. Respective spots can be made of different kinds of biomolecules, biomacromolecuels, or organic molecules. Alternatively, the spots can be made of single kind of biomolecule in each line of the array. Of course, all the spots can be same kind of substance. In the figure, although the spots are represented in circular form, they can be any kind of shapes such as a rectangular, a square, or etc.

Figure 3:
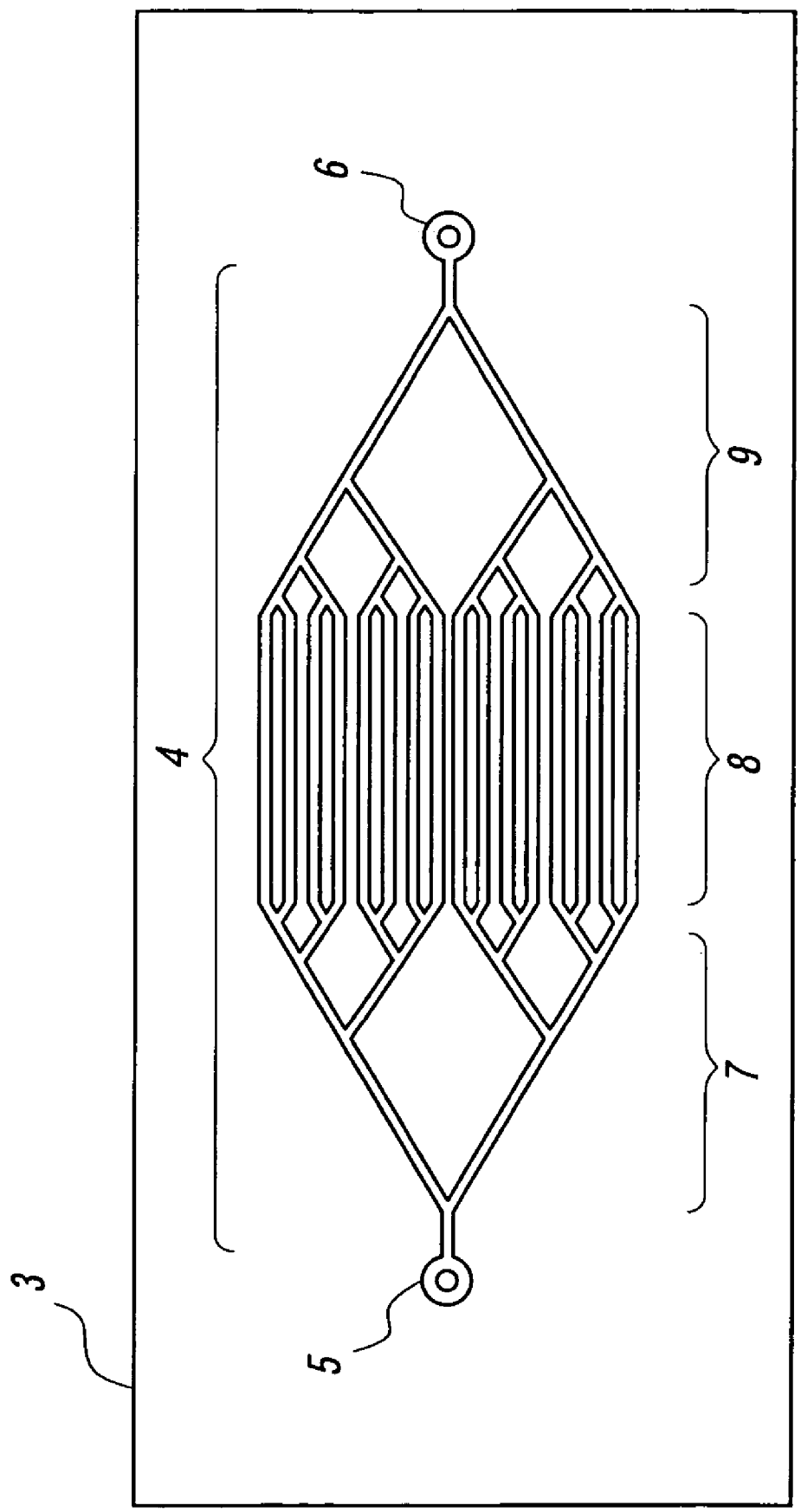
FIG. 3 is a schematic diagram representing micro flow channels in single-input and single-output.

FIG. 3 is a schematic diagram representing micro flow channels in single-input and single-output. A reaction solution is injected into the inlet 5 from a pump, a syringe, or a pipette. The solution is uniformly distributed by a liquid distribution circuit 7, i.e. minute supply flow channels and to be poured into micro reaction flow channels 8 (reaction regions). The micro reaction flow channels 8 are designed to be disposed biomolecules or biomacromolecules spots (not shown). The reaction solution would react with the biomolecules spots in the reaction flow channels 8, then to be collected and analyzed. Then the reaction solution which passes the reaction flow channels 8 flows to a collecting circuit 9, i.e. micro recovery flow channels, to be directed to an outlet 6. The reaction solution is recovered by a tube or a pump connected to the outlet 6.

Figure 4:
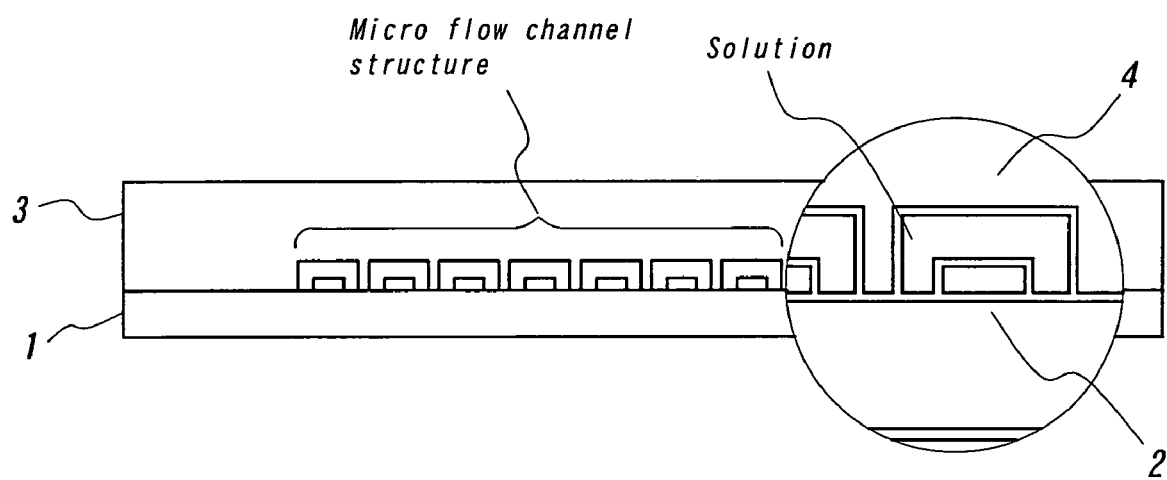
FIG. 4 is a diagram depicting a cross-sectional structure of a microchip having a substrate 1 attached a plate 3.

FIG. 4 is a diagram depicting a cross-sectional structure of a microchip having a substrate 1 attached a second substrate 3. Respective biomolecules spots 2 immobilized on a substrate 1 by the electrospray deposition method are separated by walls of micro flow channel structures, which are formed by the first substrate 1 and concave portions 4 of the palate or second substrate 3, which are bonded mutually. The microchip is designed to flow a solution on the spots 2.

How to manufacture the micro flow channels structure body that is for forming concave portions 4 in the second substrate 3 will be explained in detail.

The second substrate 3 is made of: plastics (PMMA, polycarbonate, polypropylene, or polyethylene, etc.); glass (silica grass, or optical grass, etc.); ceramics (alumina, zirconium oxide, silicon nitride, or aluminum nitride, etc.); or metal. Various forming techniques can be used for forming concave portions 4 in from of minute grooves such as a mechanical method of scraping off a part which forms concave portions using a cutting tool (a end mill or a turning tool, etc.); a method of chemical etching the concave portions using a mask made using photo-resist; a method of abrasive jet machining using the mask made using photo-resist; or a method of electric discharge machining. To produce the microchips in large quantity, following methods may be utilized. First one is a method for injection molding of plastics using a die which is made by the mechanical method. Second one is a method for injection molding of a ceramic or a metal slurry and for baking the molded product. When the dye is made of a material with high melting point such as tungsten carbide, a substrate made of glass may be pressure molded in high temperature so that concave portions 4 are formed therein.

Now, how to bond the first substrate with the second substrate 3 i.e. the micro flow channels structure body will be explained in detail.

In general, an adhesive agent is coated in thin layer to bond the first substrate 1, which supports biomolecules spots, with the second substrate 3 which will form the a micro flow channels structure body. Alternatively, following methods can be utilized for binding the first substrate with the second substrate: an optical contact method for grind surfaces of them into the surfaces with high flatness, to bond them mutually without an adhesive agent; a method for heating substrates such as a diffusion bonding; a method for applying ultrasonic vibration to substrates; and a method for applying energy beam such as laser light to a surface.

Figure 5:
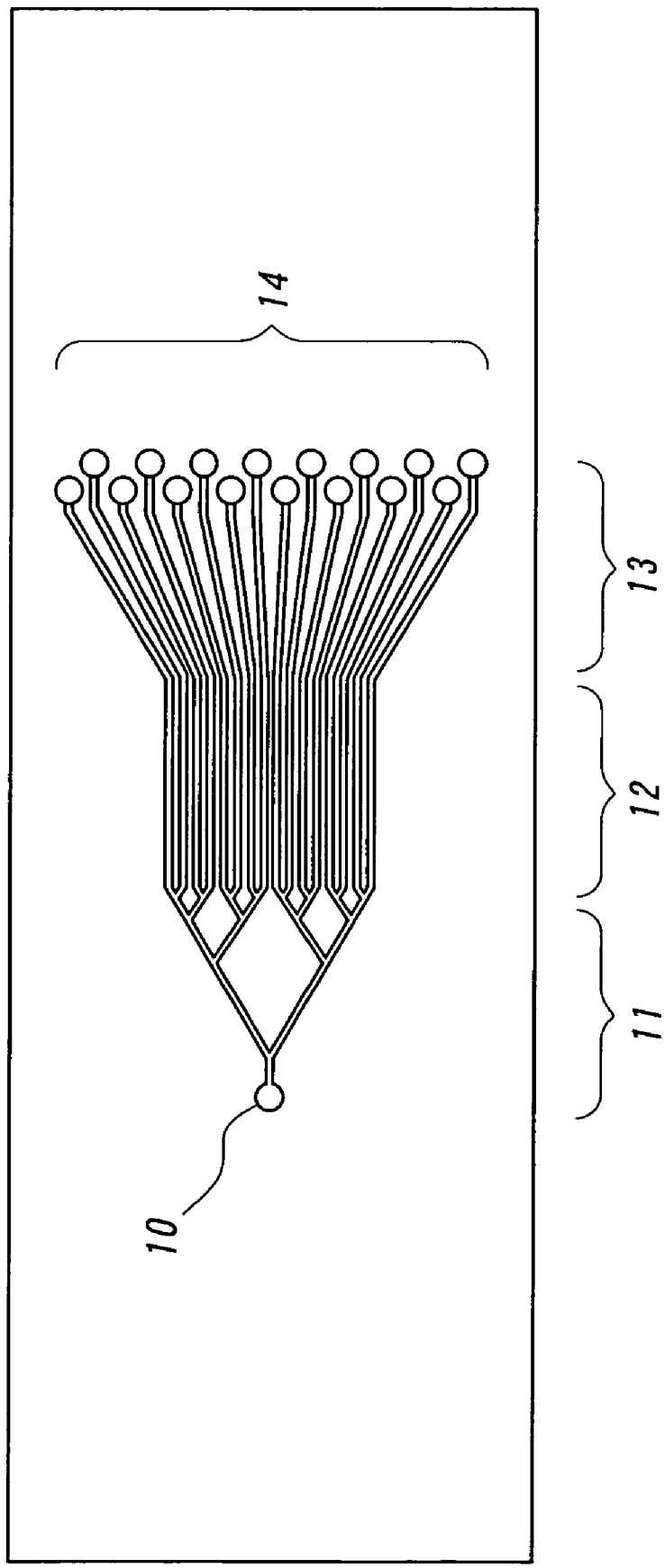
FIG. 5 is a schematic diagram showing micro flow channels in single-input and multiple-output.

FIG. 5 is a schematic diagram showing micro flow channels in single-input and multiple-output (with parallel reaction regions). A reaction liquid is injected into the inlet 10 from a pump. Then, the reaction liquid is uniformly distributed by a liquid distribution circuit 11, i.e. minute supply flow channels and to be poured into micro reaction flow channels 12 (reaction regions in parallel). The reaction liquid passes through the micro reaction flow channels 12 having biomolecules spots therein. The branched flows of the reaction liquid flows from the micro reaction channels 12 to micro recovery flow channels 13, respectively. Then the reaction liquid is poured to independent outlets 14 to be collected and recovered from respective outlets 14 by using a pump or a pipette.

Figure 6:
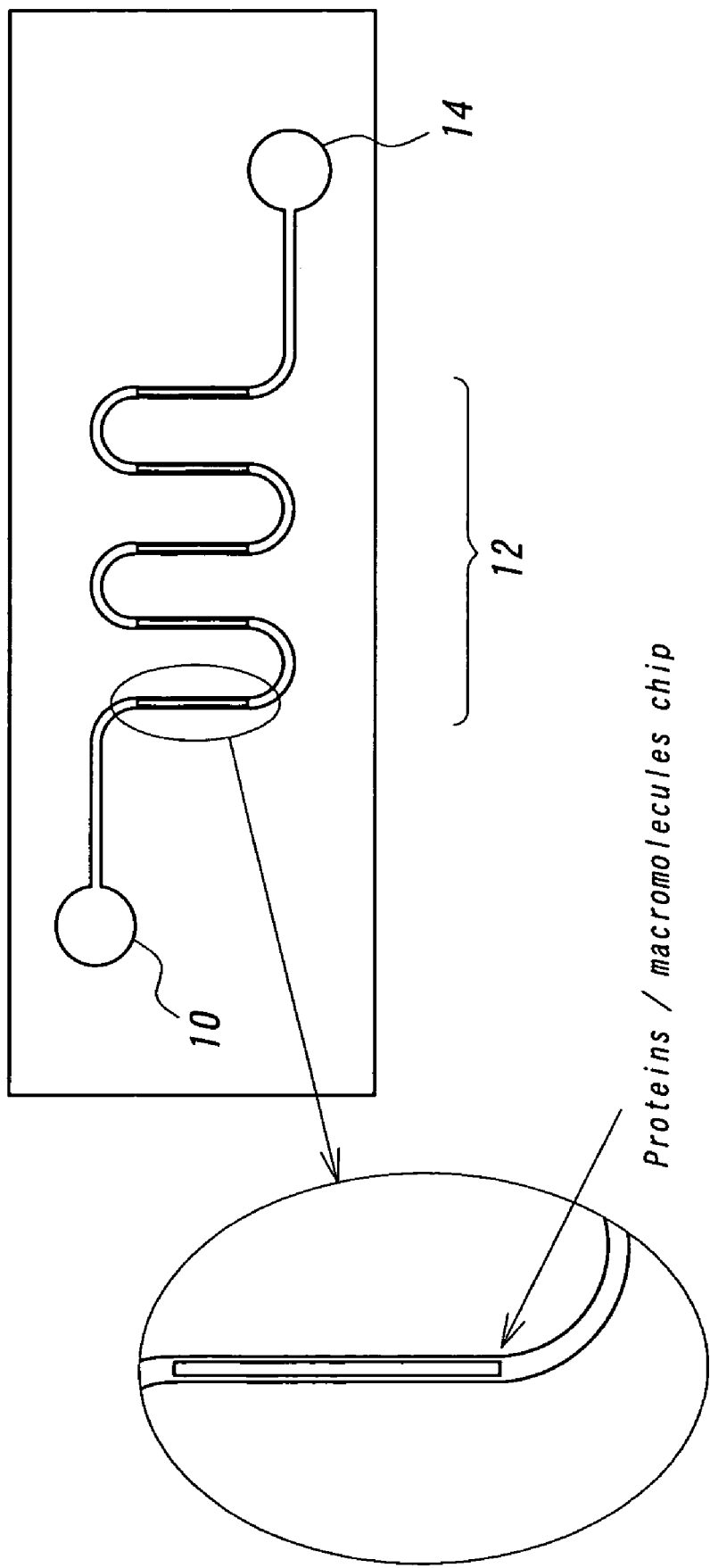
FIG. 6 is a schematic diagram illustrating micro flow channels in a consecutive reaction system.

FIG. 6 is a schematic diagram illustrating micro flow channels in a consecutive reaction system. A sample solution is injected into an inlet 10. The sample solution flows through a micro flow channel. In the middle of the channel, a plurality of macromolecules (protein) spots are intermittently disposed therein. The solution passed through sequentially the spots (i.e. micro reaction flow channel 12). Finally the solution is recovered from an outlet 14. The macromolecules spot is not necessarily in form of a round, as shown the macromolecules spot can be in a rectangular shape so that an area of reaction surfaces can be increased. The reaction solution is injected into the inlet 10 by a pump or a pipette. Then the solution flows through the reaction flow channel 12 and is recovered from the outlet 14. As shown in FIG. 6, by meandering or winding the flow channel having reaction flow channel 12, it is possible to effectively react a many number of spots and the sample solution on the microchip having only a small region for containing the channels.

FIG. 7 is a schematic diagram and its A-A' cross-sectional view depicting a micro-column having biomolecules spots which are immobilized using the electrospray deposition method. Although in this arrangement micro flow channels are formed as like as the microchip in FIG. 1., the microchip differs in following points from that in FIG. 1. Concave portions 16, which will form micro flow channels, are formed in a first substrate 15. In order to increase an area of reaction surfaces, biomolecules coating films 17 are disposed on whole walls of the concave portions 16 using the electrospray deposition method. By bonding the first substrate with a second substrate having a flat surface, micro flow channels are formed therebetween. In addition, in order to coat the walls with the macromolecules effectively, the walls of the concave portions 16 in the first substrate 15 are sloped. Accordingly, the area of reaction surfaces, which are contact surfaces between the solution and macromolecules films, may be increased. Micro reaction flow channels 19 are arranged in a mesh shape so that the area of the reaction surface can significantly be increased. Antibody, protein such as protein-A, which is used in affinity chromatography and has preferential absorption functions, or organic macromolecules can be used as biomolecules or polymer materials. The reaction flow channels i.e. reaction regions can be various shapes or patterns other than the mesh shape in FIG. 7. As described above, in FIG. 7 the first substrate 15 having the concave portions 16 including macromolecules film immobilized therein is bonded to the second substrate 18 having a flat surface without macromolecules films or spots. But, by bonding the two first substrates 15 having the concave portions 16 mutually, the area of the reaction surfaces may be increased further.

Figure 8:
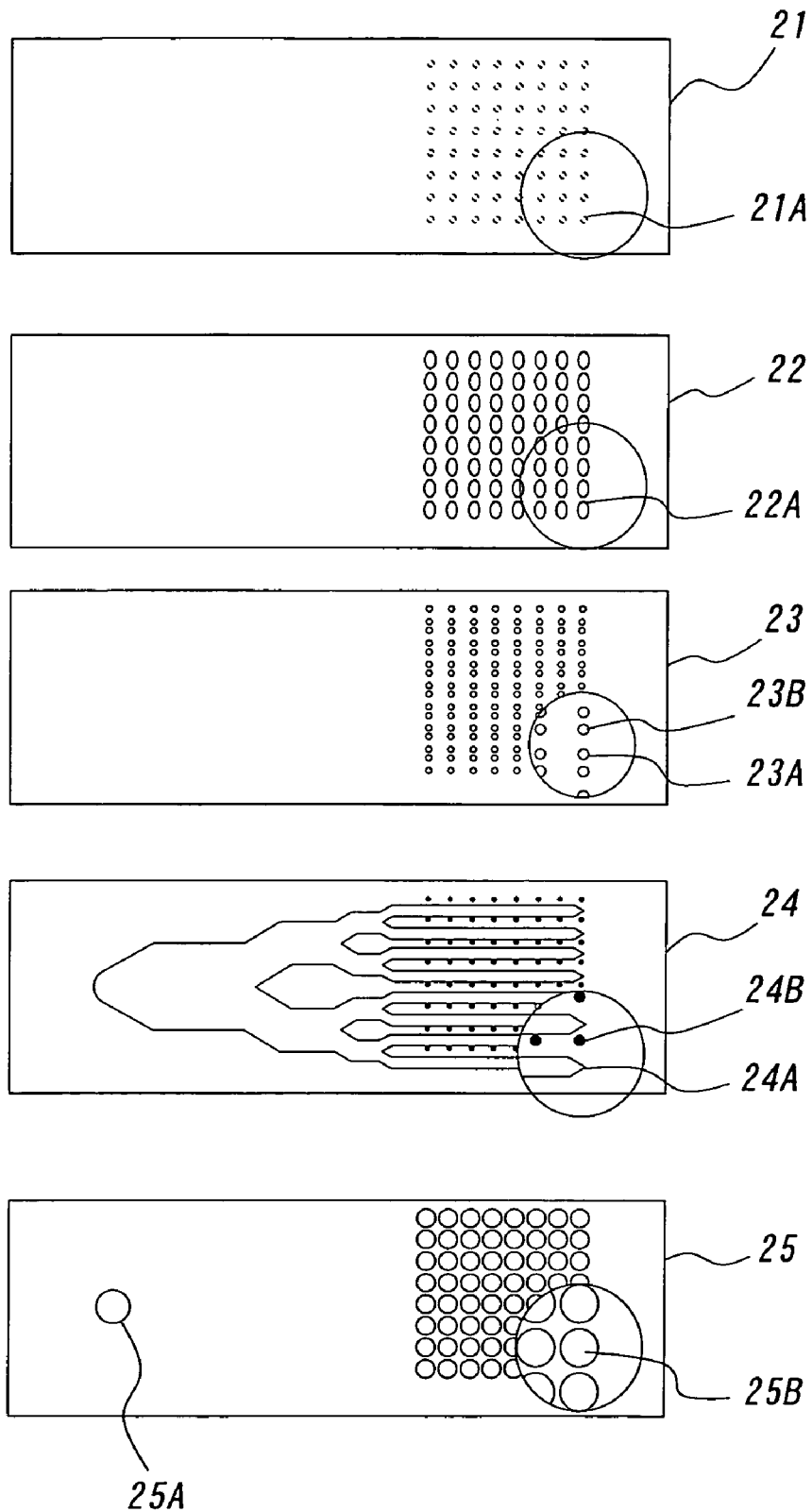
FIG. 8 is a diagram showing a structure (as one example) of a microchip system having three dimensional flow channels in a five layer (includes a substrate) structure.

By arranging flow channels in three dimensions, a sample solution ca be collected in every biomolecules spot. FIG. 8 is a diagram showing a structure of a microchip system having three dimensional flow channels in a five layer (includes a substrate) structure. This microchip is formed such that a first substrate 21, a second substrate 22, a third substrate 23, a fourth substrate 24, and a fifth substrate 25 are sequentially layered. The first substrate 21 has biomolecules spots 21A immobilized therein. The second substrate 22 has through holes 22A, which are disposed at locations corresponding to the spots 21A, which through holes 22A act as reaction flow channels (sites).

A reaction solution is injected into an inlet 25A in the fifth substrate 25 and passes through distribution flow channels 24A in the fourth substrate 24 to be poured into supply micro through holes 23A, which are located above the respective spots 21A, in the third substrate 23. Then the reaction solution flows in the respective reaction flow channels 22A of the second substrate 22.

The reaction solution passes through above the macromolecules spot 21A to be reacted with the macromolecules. The reacted solution then flows through respective recovery micro through holes 23A in the third substrate 23 and through respective recovery micro through holes 24A in the fourth substrate 24, to reach respective outlets 25B in the fifth substrate. The reacted solution is separately collected and recovered from respective outlet 25B by a pump or a pipette.

While the present invention has been described with respect to some embodiments and drawings, it is to be understood that the present invention is not limited to the above-described embodiments, and modifications and drawings, various changes and modifications may be made therein, and it is intended to cover in the appended claims all such modifications as fall within the true spirit and scope of the invention.

INDUSTRIAL APPLICABILITY

According to the present invention, it is possible to provide biomolecules microchip having a structure, which can detect bindings or reaction between a many number of proteins or DNAs and other compounds on the microchip and which can collect and recover combined or reacted compounds, to identify them.

What is claimed is:

1. A microchip, comprising a block constituting a reaction system,
wherein said reaction system includes:
a reaction region including biomolecules immobilized therein in the form of a spot(s) or a strip(s), the biomolecules being immobilized on a first substrate in a porous form that enlarges an area of contact surface between the biomolecules using an electrospray deposition method;

a supply flow channel region including a supply flow channel formed in a second substrate, the supply flow channel being arranged in a mesh shape so that an area of the reaction surface can significantly be increased, the first and second substrates being bonded so that one surface of the first and second substrates has concave portions, the electrospray deposition method further providing biomolecules-coating-films disposed on whole walls of the concave portions in order to increase an area of reaction surfaces, the reaction region formed by bonding the first and second substrates enabling original biomolecules to generate particular biomolecules in successive reactions such that a multi-step reaction can be done on the reaction region at one operation, the supply flow channel connected to the reaction region for supplying a sample solution; and a recovery flow channel region including a recovery flow channel connected to the reaction region for recovering the sample solution which passes through at least a part of the reaction region so as to uniformly feed to the snot(s) or the strip(s) in parallel;

wherein said reaction system is one of a plurality of reaction systems, the plurality of reaction systems being equal to or greater than 10 systems per $cm^2$.

2. The microchip according to claim 1, wherein said block is formed by the first and second substrates which are bonded mutually such that the reaction region, the supply flow channel and the recovery flow channel are formed at a boundary between flat surfaces of the first and second substrates; and which includes:
an inlet region connected to the supply flow channel region; and
an outlet region connected to the recovery channel region;
an inlet and an outlet for communicating the supply flow channel and recovery flow channel to outside of the microchip.

3. The microchip according to claim 1, wherein said supply flow channel region and said recovery flow channel region are arranged in two or three dimensions.

4. The microchip according to claim 2, wherein said supply flow channel or said inlet comprises a liquid flow rate controlling device for controlling the supply and/or flow rate of the sample solution,
and wherein said recovery flow channel region or said outlet comprises a liquid recovery device for collecting and recovering the sample solution which passes through the reaction region.

5. The microchip according to claim 2, wherein
said reaction system includes:
said supply flow channel region, which comprises a single input flow channel at the side of the inlet region and is separated into a plurality of supply flow channels on the side of the reaction region;
said reaction region, which comprises a plurality of paths which are respectively connected to the plurality of flow channels one by one;
said recovery flow channel region, which is comprised of a plurality of recovery flow channels which are respectively connected to the paths one by one; and
said outlet, which is a plurality of outlets which are provided for communicating respectively the plurality of recovery flow channels to outside one by one.

6. The microchip according to claim 2, wherein said reaction system includes:
   said supply flow channel region which has a single input flow channel at a side of the inlet region and is separated into a plurality of supply flow channels on a side of the reaction region;
   said reaction region, which comprises a plurality of paths which are respectively connected to the plurality of supply flow channels on a one-to-one basis with respect to reaction flow channels and supply flow channels; and
   said recovery flow channel region, which is separated into a plurality of recovery flow channels on a side of the reaction region and are interconnected into single recovery flow channel on a side of the outlet region.

7. The microchip according to claim 1, wherein said reaction system includes:
   an inlet region connected to the supply flow channel region;
   an outlet region connected to the recovery channel region;
   said supply flow channel region, which includes a plurality of supply flow channels;
   said inlet region, which includes a plurality of inlets, wherein the plurality of inlets is connected to the plurality of supply flow channels on a one-to-one basis;
   said reaction region, which includes a plurality of paths;
   said recovery flowchannel region, which includes a plurality of recovery flow channels, wherein the plurality of recovery flow channels is connected to the plurality of paths one by one; and
   said outlet region, which includes a plurality of outlets which are provided for communicating respectively the plurality of flow channels with the outside one by one.

8. The microchip according to claim 1, wherein said reaction system includes:
   an inlet region connected to the supply flow channel region;
   an outlet region connected to the recovery channel region;
   said supply flow channel region, which includes a plurality of supply flow channels;
   said inlet region, which includes a plurality of inlets which are provided for communicating respectively the plurality of flow channels with outside one by one;
   said reaction region, which comprises a plurality of paths which are respectively connected to the plurality of flow channels one by one; and
   said recovery flow channel region, which is separated into a plurality of recovery flow channels on the side of the reaction region and is interconnected into single recovery channel on the side of the outlet region.

9. The microchip according to claim 1, wherein said reaction system is one of a plurality of reaction systems, the plurality of reaction systems being equal to or greater than 100 systems per $cm^2$.

10. The microchip according to claim 1, wherein said reaction system is one of a plurality of reaction systems, the plurality of reaction systems being equal to or greater than 1000 systems per $cm^2$.

* * * * *